United States Patent [19]

Deckers et al.

[11] Patent Number: 5,569,792
[45] Date of Patent: Oct. 29, 1996

[54] HYDROGENATION OF ALDEHYDES, KETONES, CARBOXYLIC ACIDS AND ESTERS

[75] Inventors: Gregor Deckers, Xanten; Gerhardt Horn, Oberhausen, both of Germany

[73] Assignee: Hoechst Aktiengesellschaft, Germany

[21] Appl. No.: 407,754

[22] Filed: Mar. 17, 1995

Related U.S. Application Data

[62] Division of Ser. No. 172,049, Dec. 22, 1993, Pat. No. 5,453,412.

[30] Foreign Application Priority Data

Dec. 28, 1992 [DE] Germany .......................... 42 44 273.7

[51] Int. Cl.$^6$ ...................... C07C 29/141; C07C 29/145; C07C 29/149; C07C 31/12
[52] U.S. Cl. ............................................ 568/881; 568/885
[58] Field of Search ..................................... 568/881, 885

[56] References Cited

U.S. PATENT DOCUMENTS 5,155,086  10/1992  Thakur et al. .......................... 502/344

FOREIGN PATENT DOCUMENTS 8303409  10/1983  WIPO ................................... 568/885

Primary Examiner—Joseph E. Evans
Attorney, Agent, or Firm—Jordan B. Bierman; Bierman and Muserlian

[57] ABSTRACT

A copper oxide/zinc oxide/aluminum oxide catalyst which contains, per 100 parts of copper oxide, 40 to 130 parts zinc oxide, 2 to 50 parts aluminum oxide, and 1 to 4 parts soium oxide. It has a total BET surface area of 50 to 100 m$^2$/g, and 75% to 95% of the total surface area is made up by pores having radii of 9 to 1000 nm, and 5% to 25% of the total surface area is made up by pores having radii of less than 9 nm. The catalyst is useful for hydrogenation of various organic compounds.

9 Claims, No Drawings

HYDROGENATION OF ALDEHYDES, KETONES, CARBOXYLIC ACIDS AND ESTERS

This application is a division of application Ser. No. 08/172,049 filed Dec. 22, 1993, now U.S. Pat. No. 5,453,412.

This Application claims the benefit of priority of German Application P 42 44 273.7, filed Dec. 28, 1992.

The invention relates to a novel catalyst which, in addition to copper oxide, comprises zinc oxide and aluminum oxide, and to a process for its preparation. Because of its high activity and selectivity, the catalyst has proven useful in the hydrogenation of organic compounds, in particular saturated or unsaturated aldehydes, ketones, carboxylic acids, and carboxylic esters to form saturated alcohols.

BACKGROUND OF THE INVENTION

Copper-containing catalysts have wide application in chemical technology. Depending on the specific use to which they are put, they differ primarily in the materials which they contain and the quantitative composition thereof. Specifically, copper oxide/zinc oxide/aluminum oxide catalysts are the basis of modern processes for synthesizing methanol from carbon monoxide and hydrogen at low pressures.

For instance, DE-A-20 56 612 describes catalysts for preparing methanol which are compounds of the mixed crystal series $(Cu_xZn_y)Al_2(OH)_{16}CO_3.4H_2O$, where x and y are 0.5 and 5.5 and the sum of x and y is 6. The desired mixed crystals are obtained by reaction of aqueous solutions containing copper nitrate, zinc nitrate, and aluminum nitrate with basic reagents, such as aqueous sodium carbonate solution, at pH values of 4.5 to 5.5.

EP-A-01 25 689 also relates to copper oxide/zinc oxide/aluminum oxide catalysts for methanol synthesis. They are characterized by a Cu/Zn atomic ratio of 2.8 to 3.8 and an $Al_2O_3$ content of 8% to 12% by weight. They are prepared by coprecipitating copper and zinc with alkaline materials, such as alkali metals or ammonium carbonate, in the presence of the aluminum oxide component, preferably colloidally dispersed aluminum oxide or hydroxide, from their aqueous solutions. In the unreduced catalyst, 20% to 40% of the pores have a radius of from 1.0 to 3.75 nm and from 60% to 80% of the pores have a radius greater than 3.75 nm.

A further application for the above compositions is hydrogenation of organic compounds. For this type of reaction, $CuO/ZnO/Al_2O_3$ catalysts replace copper/chromium oxide catalysts (known as Adkins catalysts), the use of which has been avoided in recent times for ecological reasons, and they are in competition with the multiplicity of nickel catalysts which have been described and introduced to industry.

Hydrogenation catalysts based on copper oxide, zinc oxide and aluminum oxide wherein at least about 80% of their pore volumes consists of pores having a diameter greater than about 80Å (8 nm) are the subject of EP 04 24 061. In preferred embodiments, the catalyst powder has a surface area of at least 70 $m^2/g$, the average particle diameter is about 8 to about 28 μm and the atomic ratio of copper to zinc is about 0.2 to about 5.5. The catalysts are produced by preparing two aqueous solutions, one containing copper and zinc salts and the other containing a basic aluminum salt (for example sodium aluminate) and a basic precipitation reagent (for example soda). The two solutions are mixed with one another in a ratio such that the pH of the resulting mixture is at least about 7. The precipitated solid is subsequently filtered off and calcined. The catalyst is used for hydrogenating aldehydes, ketones, carboxylic acids, and carboxylic esters.

The known catalysts containing copper oxide, zinc oxide, and aluminum oxide have frequently been developed specifically for particular reactions; e.g. methanol synthesis or the hydrogenation of organic compounds. They can nevertheless also be used for other chemical reactions but, in such cases, do not always produce optimal results. Even different ways of carrying out the same reaction may require the provision of individualized catalysts. Experience has shown that the reaction of the same reactants under different conditions (for example in gaseous or in liquid form, on fixed catalysts, or on a catalyst suspended in the substrate) requires specially adapted catalysts. In this context it must be remembered that, in processes which are carried out on a large scale, an increase in conversion or an improvement in the selectivity in the order of even a few tenths of a percent can lead to significant economic advantages.

SUMMARY OF THE INVENTION

It is, therefore, an object of the present invention to provide catalysts of high activity and selectivity which can either be used very widely or be targeted at particular processes or process variants. In the specification and claims hereof, all parts and percentages are by weight unless otherwise stated.

This object is achieved by a catalyst comprising, per 100 parts of copper oxide, 40 to 130 parts of zinc oxide, 2 to 50 parts of aluminum oxide, and 1 to 4 parts of sodium oxide. The catalyst has a total BET surface area of 50 to 100 $m^2/g$ 75% to 95% of the total surface area consists of pores having radii of 9 to 1000 nm, and the remainder of the total surface area consists of pores having radii of less than 9 nm.

The catalyst of the invention has, in comparison with other catalysts of the same or similar qualitative compositions, appreciably higher activity and selectivity. It has proven particularly useful as a hydrogenation catalyst, and is used very successfully, for example, in the hydrogenation of saturated or unsaturated aldehydes, carboxylic acids, and carboxylic esters to form saturated alcohols.

DETAILED DESCRIPTION OF THE INVENTION

Preferably, the catalyst comprises, per 100 parts of copper oxide, 40 to 100, in particular 45 to 80, parts of the zinc oxide; 4 to 30, in particular 4 to 20, parts of aluminum oxide; and 1.5 to 3 parts of sodium oxide. The catalyst optionally contains further metals such as manganese, molybdenum, vanadium, zirconium, and/or an alkaline earth metal. Calculated as oxides, namely MnO, $MoO_3$, $V_2O_5$, $ZrO_2$, and MeO (Me is an alkaline earth metal), the proportion thereof is, per 100 parts of CuO, 0.5 to 8, preferably 1 to 6, most preferably 2 to 4 parts. The above amounts given for the metal oxides are only for the analytical description of the catalyst. They do not give the materials of which it is composed in the sense of, for example, sodium actually being present as $Na_2O$ and aluminum being present in the form of the chemical compound $Al_2O_3$.

In addition to the materials of which it is composed, the novel catalyst is characterized by its BET total surface area determined by adsorption of nitrogen. The catalyst of the invention in the calcined state, i.e. after heating for 3 to 10 hours at 350° to 480° C., preferably 400° C., has a BET surface area of 50 to 100 m²/g, in particular 60 to 80 m²/g.

The novel catalyst is further characterized by a particular pore structure. The proportion of pores having radii of 9 to 1000 nm comprises 75% to 95% of the total surface area, and the remainder of the total surface area consists of pores having radii less than 9 nm. Preferably, the proportion of pores having radii of 9 to 1000 nm is 80% to 90% and the proportion of pores having radii of less than 9 nm is 10% to 20%. Particularly useful are catalysts whose total surface area is made up to the extent of 55% to 85% by pores having radii of 15 to 1000 nm, to the extent of 5% to 25% by pores having radii of from 9 to less than 15 nm, and to the extent of 10 to 20% by pores smaller than 9 nm. The above pore sizes are all based on the calcined catalyst.

The pore-radius distribution is determined by two methods which supplement each other. The distribution of small radii (up to about 30 nm) is determined by evaluation of the $N_2$ desorption isotherm by means of the Kelvin equation as described in C. Pierce, J. Phys. Chem. 57 (1953), 149 ff. Pore radii of about 4 nm to about 0.1 mm are determined by the mercury penetration method of H. L. Ritter and L. C. Drake, Ind. Eng. Chem. analyt. Ed. 17 (1945), 782.

Pores of the above size and size distribution can be achieved by a high $CO_2$-content (in the form of carbonate) in the catalyst precursor, i.e. in the product dried at from 50° to 95° C. but not yet calcined. It has proven advantageous for this precursor to contain, per 100 parts of copper oxide, 32 to 45, preferably 36 to 40, parts of $CO_2$.

The novel catalyst can be prepared, for example, by precipitation of the components from an aqueous solution under conditions which ensure the high $CO_2$-content which is advantageous in the catalyst precursor. A particularly suitable process comprises forming an aluminum hydroxide suspension by reaction of an aluminum salt solution with an alkali metal carbonate or alkali metal hydrogen carbonate solution, simultaneously but separately adding, at 80° to 100° C. while stirring, a solution containing copper and zinc salts and a solution of alkali metal carbonate or alkali metal hydrogen carbonate. The solid formed is filtered off, washed, dried at 50° to 95° C., and then calcined at 350° to 480° C. The aluminum, copper, and zinc salts used are compounds readily soluble in water which are derived from inorganic or even organic acids, such as halides, sulfates, or acetates. Because of their high solubility, their chemical inertness, the comparative ease of removal of the anion, and their general availability, nitrates are preferred. Precipitants used are alkali metal carbonates and/or hydrogen carbonates, in particular their sodium salts. The concentration of the salts in the solutions may vary over a wide range. The aluminum salt solution contains, per liter of solution, the aluminum salt in an amount which corresponds to 20 to 100, preferably 30 to 90, and in particular 40 to 80, grams of $Al_2O_3$. The concentrations of copper and zinc in their joint solution are from 10 to 100 g of Cu and from 5 to 80 g of Zn per liter of solution. The preferred precipitant, sodium carbonate, is advantageously used as a solution which contains 50 to 150 g of $Na_2CO_3$ per liter; however, the use of lower sodium carbonate concentrations is not excluded.

The aluminum hydroxide is precipitated by running the aluminum salt solution at 20° to 90° C. over 2 to 10 minutes into an alkali metal carbonate and/or alkali metal hydrogen carbonate solution which is at 20° to 100° C., preferably 30° to 80° C., while stirring vigorously. The ratio of aluminum salt to precipitant is selected so that the pH of the suspension is 6.5 to 8.5 after the reaction is complete. Subsequently the temperature is adjusted to 80° to 100° C., preferably 90° to 98° C., and the alkali metal carbonate and/or alkali metal hydrogen carbonate solution and the copper salt/zinc salt solution, each heated to 80° to 100° C., preferably from 90° to 98° C., are added simultaneously but separately over 10 to 30 minutes while stirring vigorously. The rates of addition of the two solutions are adjusted so that the pH of the suspension is 7.5 to 8.0. As soon as the addition of the two solutions is complete, the suspension is filtered. The filter residue is washed, dried at 50° to 95° C., and subsequently calcined at 350° to 480° C., preferably 400° to 460° C. The shaping of the material, for example by extrusion or tableting, can be carried out before drying or after calcination. The catalyst is activated by reduction at 130° to 200° C. preferably 150° to 180° C. The reduction is conducted in a separate reactor or directly in the hydrogenation reactor.

The novel catalyst is successfully used for hydrogenating organic compounds, preferably for hydrogenating saturated or unsaturated aldehydes, ketones, carboxylic acids, or carboxylic esters. It has proven particularly useful in the hydrogenation of unsaturated and saturated aldehydes in the gaseous phase.

The examples below illustrate the invention, but do not limit it.

EXAMPLE 1

Catalyst Preparation

A solution of 925 g of $Al(NO_3)_3.9H_2O$ in 3 liters of water at room temperature is introduced within 3 minutes into a solution heated to 70° C. of 580 g of soda in 5.5 liters of water with vigorous stirring. While continuing stirring, the temperature of the resulting suspension is raised to 95° C. over a period of about 10 minutes. A solution heated to 95° C. of 2249.2 g of $Cu(NO_3)_2.3H_2O$ and 1755.4 g of $Zn(NO_3)_2.6H_2O$ in 10 liters of water and a solution also heated to 95° C. of 2340 g of $Na_2CO_3$ in 18 liters of water are added simultaneously but separately over a period of 15 minutes. During the reaction, the suspension is maintained at a pH of 7.5 to 8.0. Subsequently, the suspension is stirred for a further 2 minutes and then filtered. The filter residue is continuously washed for 80 minutes with 80 liters of water and, after shaping by extrusion or by spray drying, is dried at no more than 100° C. to a water content of less than 5%. The dried uncalcined catalyst precursor comprises 38.8% CuO (31% by weight Cu). It also contains 65 parts ZnO, 17 parts $Al_2O_3$ 2.0 parts $Na_2O$, and 38.6 parts $CO_2$ per 100 parts CuO.

In a subsequent process step, the precursor is heated in a stream of nitrogen or air (200 liters/h) to 430° C. and maintained at this temperature for a further 3 hours. The resulting calcined product comprises 51% CuO, and 65 parts ZnO, 17 parts $Al_2O_3$, 2.0 parts $Na_2$, and 1.5 parts $CO_2$ per 100 parts CuO. It has a total BET surface area of 68 m²/g; 84% of the surface area is made up by pores having radii greater than 9 nm but less than 1000 nm, and 16% is made up by pores having radii less than 9 nm. The calcined product can be used in extruded or tableted form as a fixed-bed catalyst.

EXAMPLE 2

Hydrogenation of n-butyraldehyde 250 ml of the catalyst of Example 1 which has been tableted is reduced in a reaction tube at 160° C. with 400 liters/hour of a $H_2/N_2$ mixture containing 3% by volume of H₂ until no more water is formed. Subsequently, a mixture of 250 ml of gaseous n-butyraldehyde and 710 liters of hydrogen per hour are passed over the catalyst at 145° C. and a gauge pressure of 0.3 MPa. The excess hydrogen is recirculated.

The hydrogenation product has the following composition, determined by gas chromatography:

| n-butanol | | 99.8% by weight |
|---|---|---|
| n-butyraldehyde | < | 0.05% by weight |
| butyl butyrate | < | 0.05% by weight |
| 2-ethylhexanol | < | 0.05% by weight |
| di-n-butyl ether | ≦ | 10.0 ppm by weight |

Particularly noteworthy in comparison with the prior art is the exceptionally low formation of byproducts when using the catalysts of the invention.

EXAMPLE 3

Hydrogenation of 2-ethylhexenal 3 liters of the catalyst of Example 1 which has been tableted is reduced as in Example 2. Subsequently, a gaseous mixture of 1500 ml/h of 2-ethylhexenal (liquid) and 4.4 standard m³/h of hydrogen is passed over the catalyst at 145° C. and a gauge pressure of 50 kPa. The starting material and reaction product have the following compositions, determined by gas chromatography.

| | Starting material (% by weight) | Reaction product (% by weight) |
|---|---|---|
| C₇/C₈ hydrocarbons | ≦0.1 | ≦0.1 |
| n/i-butanal | 3–4 | — |
| n/i-butanol | 0.5–1.5 | 3.5–4.5 |
| 2-ethylhexenal | 90–91.5 | 0.1 |
| 2-ethylhexanal | about 1 | 0.2–0.3 |
| 2-ethylhexanol | 3.5–4.5 | 95–97 |
| higher boiling-point components (such as acetals, diols) | 2–3 | 0.5–0.8 |

EXAMPLE 4 (COMPARATIVE)

Hydrogenation of n-butyraldehyde

In this example, a catalyst of the prior art is used. It comprises 47.5% Cu, and 49.5 parts ZnO, 8.4 parts Al₂O₃, and 0.12 parts Na₂O per 100 parts CuO. Its total BET surface area is 128 g/m²; 85% of the surface area is made up of pores having radii equal to or less than 15 nm.

250 ml of the tableted catalyst is reduced in a tube reactor, as in Example 2. Subsequently, a gaseous mixture of 250 ml/h of n-butyraldehyde (liquid) and 710 liters of hydrogen per hour is passed over the catalyst at 145° C. and a gauge pressure of 0.3 MPa. The excess hydrogen is recirculated.

The hydrogenation product has the following composition by gas chromatography:

| n-butanol | 99.5–99.6% by weight |
|---|---|
| n-butyraldehyde | 0.2–0.3% by weight |
| butyl butyrate | about 0.02% by weight |
| di-n-butyl ether | about 100 ppm by weight |

While only a limited number of specific embodiments of the present invention has been expressly disclosed, it is, nonetheless to be broadly construed and not to be limited except by the character of the claims appended hereto.

What we claim is:

1. A method of hydrogenating organic compounds selected from the group consisting of aldehydes, ketones, carboxylic acids, carboxylic esters, and mixtures thereof, said method comprising, contacting said compounds, under hydrogenation conditions, with a catalyst comprising, per 100 parts copper oxide, 40 to 130 parts zinc oxide, 2 to 50 parts aluminum oxide, and 1 to 4 parts sodium oxide, said catalyst having a total BET surface area of 50 to 110 m²/g, wherein 75% to 95% of said total surface area is made up by pores having radii of 9 to 1000 nm, the remainder of said total surface area being pores having radii of less than 9 nm.

2. The method of claim 1 wherein said catalyst comprises, per 100 parts by weight of copper oxide, 40 to 100 parts zinc oxide, 4 to 30 parts aluminum oxide, and 1.5 to 3 parts sodium oxide.

3. The method of claim 2 wherein said catalyst comprises, per 100 parts of copper oxide, 45 to 80 parts zinc oxide, and 4 to 20 parts aluminum oxide.

4. The method of claim 1 wherein said catalyst comprises, per 100 parts copper oxide, 0.5 to 8 parts of a metal selected from the group consisting of manganese, molybdenum, vanadium, zirconium, alkaline earths, and mixtures thereof, said metal being calculated as MnO, MoO₃, V₂O₅, ZrO₂, and MeO, wherein Me is alkaline earth.

5. The method of claim 4 wherein said catalyst contains, per 100 parts copper oxide, 1 to 6 parts of said metal.

6. The method of claim 5 wherein said catalyst comprises, per 100 parts copper oxide, 2 to 4 parts of said metal.

7. The method of claim 1 wherein, in said catalyst, said BET surface area is 60 to 80 m²/g.

8. The method of claim 1 wherein, in said catalyst, 80% to 90% of said total BET surface area is made up of pores having radii of 9 to 1000 nm, and 10 to 20% of said total BET surface area is made up by pores having radii less than 9 nm.

9. The method of claim 1 wherein, in said catalyst, 55% to 85% of said total BET surface is made up by pores having radii of 15 to 1000 nm, 5% to 25% of said total BET surface area is made up by pores having radii of 9 to less than 15 nm, and 10% to 20% of said total BET surface area is made up by pores having radii less than 9 nm.

* * * * *